United States Patent
Kamon

(10) Patent No.: US 12,059,123 B2
(45) Date of Patent: Aug. 13, 2024

(54) MEDICAL IMAGE PROCESSING APPARATUS, MEDICAL IMAGE PROCESSING METHOD, PROGRAM, AND ENDOSCOPE SYSTEM

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 685 days.

(21) Appl. No.: 17/180,638

(22) Filed: Feb. 19, 2021

(65) Prior Publication Data
US 2021/0174115 A1 Jun. 10, 2021

Related U.S. Application Data

(63) Continuation of application No. PCT/JP2019/034790, filed on Sep. 4, 2019.

(30) Foreign Application Priority Data

Sep. 11, 2018 (JP) .................... 2018-169399

(51) Int. Cl.
*A61B 1/00* (2006.01)
*G06F 18/213* (2023.01)
(Continued)

(52) U.S. Cl.
CPC ...... *A61B 1/000094* (2022.02); *G06F 18/213* (2023.01); *G06T 7/0012* (2013.01);
(Continued)

(58) Field of Classification Search
CPC ............ A61B 1/000094; G06F 18/213; G06T 7/0012; G06T 7/11; G06T 2207/10068; G06V 10/25; G06V 10/56
See application file for complete search history.

(56) References Cited

U.S. PATENT DOCUMENTS 8,681,208 B2 3/2014 Yoshino
9,207,179 B2 12/2015 Ishihara
(Continued)

FOREIGN PATENT DOCUMENTS

CN 102247116 11/2011
CN 102740757 10/2012
(Continued)

OTHER PUBLICATIONS

"Search Report of Europe Counterpart Application", issued on Sep. 9, 2021, pp. 1-8.
(Continued)

*Primary Examiner* — Zhitong Chen
(74) *Attorney, Agent, or Firm* — JCIPRNET

(57) ABSTRACT

The present invention aims to provide a medical image processing apparatus, a medical image processing method, a program, and an endoscope system that report a region of interest without interrupting observation of a medical image. The above problem is solved by a medical image processing apparatus including: an emphasis processing unit that emphasizes a position of a region of interest included in a plurality of medical images sequentially displayed on a display unit; and a transition time setting unit that sets a transition time in accordance with a feature quantity of the region of interest, in which the emphasis processing unit emphasizes the position of the region of interest at a first emphasis level and, after the transition time has elapsed from emphasis at the first emphasis level, emphasizes the position of the region of interest at a second emphasis level relatively lower than the first emphasis level.

24 Claims, 12 Drawing Sheets

(51) Int. Cl.
*G06T 7/00* (2017.01)
*G06T 7/11* (2017.01)
*G06V 10/25* (2022.01)
*G06V 10/56* (2022.01)

(52) U.S. Cl.
CPC ............... *G06T 7/11* (2017.01); *G06V 10/25* (2022.01); *G06V 10/56* (2022.01); *G06T 2207/10068* (2013.01)

(56) References Cited

U.S. PATENT DOCUMENTS

| | | | |
|---|---|---|---|
| 9,990,710 | B2 | 6/2018 | Jeon |
| 10,863,893 | B2 | 12/2020 | Imaizumi et al. |
| 2012/0274754 | A1 | 11/2012 | Tsuruoka |
| 2015/0276602 | A1 | 10/2015 | Ishihara |
| 2016/0093046 | A1 | 3/2016 | Jeon |
| 2018/0249900 | A1 | 9/2018 | Imaizumi et al. |
| 2019/0069757 | A1* | 3/2019 | Iwaki ................... A61B 1/0005 |

FOREIGN PATENT DOCUMENTS

| | | | | |
|---|---|---|---|---|
| CN | 104853666 | | 8/2015 | |
| CN | 105468891 | | 4/2016 | |
| CN | 108348145 | | 7/2018 | |
| EP | 3360461 | | 8/2018 | |
| JP | 2006255021 | | 9/2006 | |
| JP | 2006255021 | A * | 9/2006 | ............... A61B 5/00 |
| JP | 2011160848 | | 8/2011 | |
| WO | 2014091964 | | 6/2014 | |
| WO | 2017081976 | | 5/2017 | |
| WO | 2017104192 | | 6/2017 | |
| WO | 2017203560 | | 11/2017 | |

OTHER PUBLICATIONS

"Office Action of Japan Counterpart Application", issued on May 13, 2022, with English translation thereof, p. 1-p. 11.

"International Search Report (Form PCT/ISA/210) of PCT/JP2019/034790," mailed on Oct. 15, 2019, with English translation thereof, pp. 1-5.

"Written Opinion of the International Searching Authority (Form PCT/ISA/237) of PCT/JP2019/034790," mailed on Oct. 15, 2019, with English translation thereof, pp. 1-11.

"Office Action of China Counterpart Application", issued on Feb. 27, 2024, with English translation thereof, pp. 1-23.

"Office Action of China Counterpart Application", issued on Aug. 25, 2023, with English translation thereof, pp. 1-25.

* cited by examiner

MEDICAL IMAGE PROCESSING APPARATUS, MEDICAL IMAGE PROCESSING METHOD, PROGRAM, AND ENDOSCOPE SYSTEM

CROSS-REFERENCE TO RELATED APPLICATIONS

The present application is a Continuation of PCT International Application No. PCT/JP2019/034790 filed on Sep. 4, 2019 claiming priority under 35 U.S.C § 119(a) to Japanese Patent Application No. 2018-169399 filed on Sep. 11, 2018. Each of the above applications is hereby expressly incorporated by reference, in its entirety, into the present application.

BACKGROUND OF THE INVENTION

1. Field of the Invention

The present invention relates to a medical image processing apparatus, a medical image processing method, a program, and an endoscope system, and particularly to a technique for reporting a region of interest in a time-series image.

2. Description of the Related Art

In the medical field, inspections are performed by using an endoscope system. In recent years, a technique for automatically detecting a region of interest such as a lesion from an endoscopic image captured by an endoscope-scope is expected to lead to prevention of missing of a lesion.

As a method for reporting the automatically detected result to a surgeon, for example, there is emphasis display by superposing a figure on the region of interest in the image.

JP2011-160848A discloses an image processing apparatus that, when performing display manner setting processing of a display image generated based on a normal light image having information within a wavelength band of white light, detects a region of interest based on a feature quantity of a pixel within a specific wavelength band light image, performs processing for setting an elapsed time based on a detection result of the region of interest, and, until the elapsed time elapses, displays a display image for which alert information for the region of interest is set. A movement amount in the normal light image is detected, and, as the detected movement amount is larger, a shorter overtime is set.

In addition, WO2017/203560A discloses an endoscopic image processing apparatus that detects a region of interest from sequentially input observation images of a subject, and, if the region of interest is continuously detected, performs emphasis processing of a position corresponding to the region of interest, on the observation images of the subject that are input after a first period elapses from a time point of a start of detection of the region of interest. The first period is set based on at least one of position information or size information of the region of interest in the observation images.

SUMMARY OF THE INVENTION

Since the image processing apparatus according to JP2011-160848A displays the display image for which alert information is set until the set elapsed time elapses, even if the region of interest disappears from a screen, the alert information may be continuously displayed. Such alert information may unfortunately interrupt image observation. In addition, even if the shorter overtime is set as the movement amount is larger, unfortunately, it is not possible to emphasize the region of interest that tends to be missed.

Furthermore, in the endoscopic image processing apparatus according to WO2017/203560A, the emphasis processing is not performed immediately after detection of the region of interest, and thus, unfortunately, it is not possible to prevent the region of interest from being missed. In addition, it is likely that the emphasis processing is performed after a surgeon has found the region of interest, and unfortunately, it may interrupt image observation.

The present invention has been made in view of such circumstances, and an object is to provide a medical image processing apparatus, a medical image processing method, a program, and an endoscope system that report a region of interest without interrupting observation of a medical image.

In order to achieve the above object, a medical image processing apparatus according to an aspect is a medical image processing apparatus including: an emphasis processing unit that emphasizes a position of a region of interest included in a plurality of medical images sequentially displayed on a display unit; and a transition time setting unit that sets a transition time in accordance with a feature quantity of the region of interest, in which the emphasis processing unit emphasizes the position of the region of interest at a first emphasis level and, after the transition time has elapsed from emphasis at the first emphasis level, emphasizes the position of the region of interest at a second emphasis level relatively lower than the first emphasis level.

According to this aspect, the position of the region of interest is emphasized at the first emphasis level and, after the transition time has elapsed, is emphasized at the second emphasis level relatively lower than the first emphasis level. Thus, the region of interest can be reported without interrupting observation of the medical images.

According to the present invention, the region of interest can be reported without interrupting observation of the medical images.

The medical image processing apparatus preferably further includes: an image acquiring unit that acquires the plurality of medical images; a region-of-interest detecting unit that detects the region of interest from the medical images; and a feature quantity calculating unit that calculates the feature quantity of the region of interest. Thus, the plurality of medical images, the region of interest, and the feature quantity can be acquired appropriately.

The medical image processing apparatus preferably further includes: a display control unit that causes the display unit to sequentially display the plurality of medical images. Thus, the plurality of medical images in which the region of interest is emphasized can be sequentially displayed on the display unit.

The feature quantity is preferably calculated based on visibility of the region of interest. Thus, the transition time can be set appropriately.

The transition time setting unit preferably sets the transition time to a longer time as the visibility of the region of interest is relatively lower. Thus, the transition time can be set appropriately.

The feature quantity is preferably calculated based on a size of the region of interest in the medical images. Thus, the transition time can be set appropriately.

The transition time setting unit preferably sets the transition time to a longer time as the size of the region of interest in the medical images is relatively smaller. Thus, the transition time can be set appropriately.

The feature quantity is preferably calculated based on a position of the region of interest in the medical images. Thus, the transition time can be set appropriately.

The transition time setting unit preferably sets the transition time to a longer time as the position of the region of interest in the medical images is relatively closer to a periphery. Thus, the transition time can be set appropriately.

The feature quantity is preferably calculated based on luminance of the region of interest or a difference between the luminance of the region of interest and luminance of an outside region of the region of interest. Thus, the transition time can be set appropriately.

The transition time setting unit preferably sets the transition time to a longer time as the luminance of the region of interest is lower, or the difference between the luminance of the region of interest and the luminance of the outside region of the region of interest is smaller. Thus, the transition time can be set appropriately.

The feature quantity is preferably calculated based on color information of the region of interest or a difference between the color information of the region of interest and color information of an outside region of the region of interest. Thus, the transition time can be set appropriately.

The transition time setting unit preferably sets the transition time to a longer time as a difference between a color space of the region of interest and a color space of the outside region of the region of interest is smaller. Thus, the transition time can be set appropriately.

The feature quantity is preferably calculated based on a movement amount of the region of interest or a movement direction of the region of interest. Thus, the transition time can be set appropriately.

The transition time setting unit preferably sets the transition time to a longer time as the movement amount of the region of interest is larger.

Thus, the transition time can be set appropriately.

The transition time setting unit preferably resets the transition time in accordance with the feature quantity of the region of interest from emphasis at the first emphasis level until the transition time elapses. Thus, the transition time can be set appropriately.

The emphasis processing unit preferably places emphasis at the first emphasis level from emphasis at the first emphasis level until the transition time elapses. Thus, the position of the region of interest can be emphasized appropriately.

The emphasis processing unit preferably places emphasis while relatively, gradually decreasing an emphasis level from emphasis at the first emphasis level until the transition time elapses. Thus, the position of the region of interest can be emphasized appropriately.

The emphasis processing unit preferably ends emphasis when a fixed time elapses from emphasis at the second emphasis level. Thus, the region of interest can be emphasized without interrupting observation of the medical images.

The emphasis processing unit preferably places emphasis at the second emphasis level from emphasis at the second emphasis level until the fixed time elapses. Thus, the position of the region of interest can be emphasized appropriately.

The emphasis processing unit preferably places emphasis while relatively, gradually decreasing an emphasis level from emphasis at the second emphasis level until the fixed time elapses. Thus, the position of the region of interest can be emphasized appropriately.

In order to achieve the above object, an endoscope system according to an aspect is an endoscope system including: the above medical image processing apparatus; an endoscope that captures the plurality of medical images; and the display unit.

According to this aspect, the region of interest can be reported without interrupting observation of the medical images.

In order to achieve the above object, a medical image processing method according to an aspect is a medical image processing method including: an emphasis processing step for enhancing a position of a region of interest included in a plurality of medical images sequentially displayed on a display unit; and a transition time setting step for setting a transition time in accordance with a feature quantity of the region of interest, in which, in the emphasis processing step, the position of the region of interest is emphasized at a first emphasis level and, after the transition time has elapsed from emphasis at the first emphasis level, the position of the region of interest is emphasized at a second emphasis level relatively lower than the first emphasis level.

According to this aspect, the region of interest can be reported without interrupting observation of the medical images. A program causing a computer to execute the above medical image processing method is also included in this aspect.

According to the present invention, the region of interest can be reported without interrupting observation of the medical images.

DESCRIPTION OF THE PREFERRED EMBODIMENTS

Hereinafter, preferred embodiments will be described in detail with reference to the accompanying drawings.

Overall Configuration of Endoscope System

Figure 1:
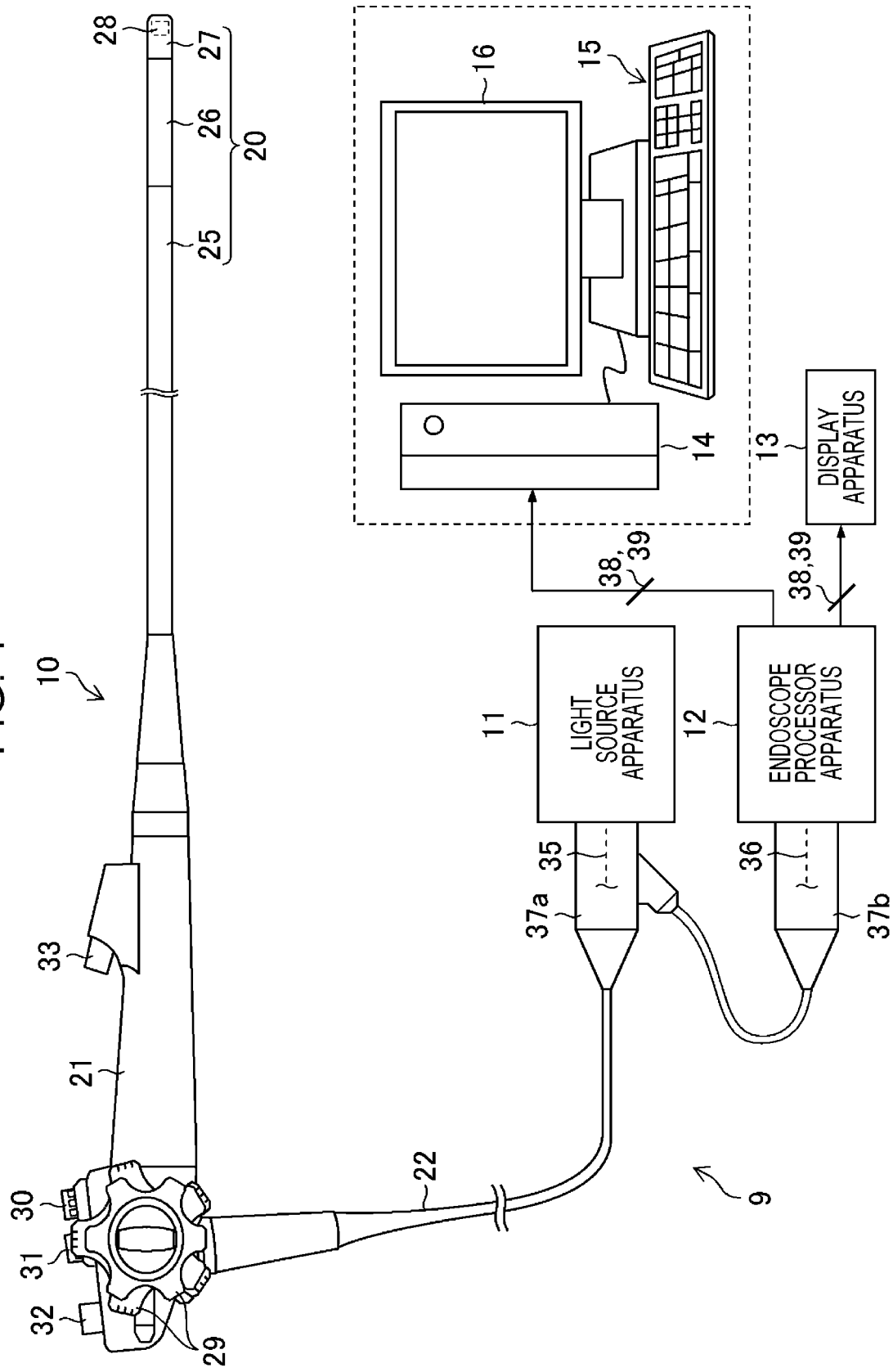
FIG. 1 illustrates an overview of an overall configuration of an endoscope system.

FIG. 1 illustrates an overview of an overall configuration of an endoscope system 9 including a medical image processing apparatus according to an embodiment. As illustrated in FIG. 1, the endoscope system 9 includes an endoscope 10, which is an electronic endoscope, a light source apparatus 11, an endoscope processor apparatus 12, a display apparatus 13, a medical image processing apparatus 14, an operating unit 15, and a display 16.

The endoscope 10 corresponds to a time-series image acquiring unit that acquires a time-series image including a photographic subject image and is a flexible endoscope, for example. The endoscope 10 has an insertion part 20, a handheld operating unit 21, and a universal cord 22. The insertion part 20 is inserted into a subject and has a distal end and a base end. The handheld operating unit 21 is disposed continuously with the base end side of the insertion part 20 and held by a surgeon to perform various operations. The universal cord 22 is disposed continuously with the handheld operating unit 21.

The entire insertion part 20 is formed to have a small diameter and an elongated shape. The insertion part 20 is constituted by a soft part 25, a bending part 26, and a distal end part 27, which are disposed continuously with each other in this order from the base end side to the distal end side. The soft part 25 has flexibility. The bending part 26 is bendable by an operation of the handheld operating unit 21. An imaging optical system (objective lens), an imaging element 28, and the like, which are not illustrated, are incorporated in the distal end part 27.

The imaging element 28 is an imaging element of a complementary metal oxide semiconductor (CMOS) type or a charge coupled device (CCD) type. Image light of a part to be observed is incident on an imaging surface of the imaging element 28 through an observation window and the objective lens. The observation window, which is not illustrated, is open on a distal end surface of the distal end part 27, and the objective lens, which is not illustrated, is disposed behind the observation window. The imaging element 28 captures the image light of the part to be observed, which is incident on the imaging surface (converts the image light into an electric signal) and outputs an image signal.

The handheld operating unit 21 is provided with various operating members to be operated by a surgeon. Specifically, the handheld operating unit 21 is provided with two types of bending operation knobs 29 to be used for a bending operation of the bending part 26, an air/water supply button 30 for air supply/water supply operations, and a suction button 31 for a suction operation. The handheld operating unit 21 is further provided with a still image pick-up command unit 32 for issuing a command for capturing a still image 39 of the part to be observed and a treatment tool introduction port 33 for inserting a treatment tool (not illustrated) into a treatment tool insertion path (not illustrated) that penetrates through the insertion part 20.

The universal cord 22 is a connection cord for connecting the endoscope 10 to the light source apparatus 11. The universal cord 22 contains a light guide 35 that penetrates through the insertion part 20, a signal cable 36, and a fluid tube (not illustrated). In addition, an end portion of the universal cord 22 is provided with a connector 37a that is connected to the light source apparatus 11 and a connector 37b that branches off from the connector 37a and is connected to the endoscope processor apparatus 12.

Since the connector 37a is connected to the light source apparatus 11, the light guide 35 and the fluid tube (not illustrated) are inserted into the light source apparatus 11. Thus, through the light guide 35 and the fluid tube (not illustrated), necessary illumination light, water, and gas are supplied from the light source apparatus 11 to the endoscope 10. As a result, the part to be observed is irradiated with the illumination light from an illumination window (not illustrated) on the distal end surface of the distal end part 27. In accordance with a pressing operation on the above-described air/water supply button 30, the gas or water is injected from an air/water supply nozzle (not illustrated) on the distal end surface of the distal end part 27 to the observation window (not illustrated) on the distal end surface.

Since the connector 37b is connected to the endoscope processor apparatus 12, the signal cable 36 is electrically connected to the endoscope processor apparatus 12. Thus, through the signal cable 36, an image signal of the part to be observed is output from the imaging element 28 of the endoscope 10 to the endoscope processor apparatus 12, and also, a control signal is output from the endoscope processor apparatus 12 to the endoscope 10.

The light source apparatus 11 supplies the illumination light through the connector 37a to the light guide 35 of the endoscope 10. As the illumination light, light in various wavelength ranges in accordance with an observation purpose, such as white light (light in a white wavelength range or light in a plurality of wavelength ranges), light in one or more specific wavelength ranges, or a combination thereof is selected. Note that the specific wavelength range is narrower than the white wavelength range.

A first example of the specific wavelength range is, for example, a blue range or a green range in a visible range. The wavelength range of the first example includes a wavelength range of greater than or equal to 390 nm and less than or equal to 450 nm or greater than or equal to 530 nm and less than or equal to 550 nm, and light of the first example has a peak wavelength in the wavelength range of greater than or equal to 390 nm and less than or equal to 450 nm or greater than or equal to 530 nm and less than or equal to 550 nm.

A second example of the specific wavelength range is, for example, a red range in a visible range. The wavelength range of the second example includes a wavelength range of greater than or equal to 585 nm and less than or equal to 615 nm or greater than or equal to 610 nm and less than or equal to 730 nm, and light of the second example has a peak wavelength in the wavelength range of greater than or equal to 585 nm and less than or equal to 615 nm or greater than or equal to 610 nm and less than or equal to 730 nm.

A third example of the specific wavelength range includes a wavelength range in which oxidized hemoglobin and reduced hemoglobin have different absorption coefficients, and light of the third example has a peak wavelength in the wavelength range in which oxidized hemoglobin and reduced hemoglobin have different absorption coefficients. The wavelength range of the third example includes a wavelength range of 400±10 nm, 440±10 nm, 470±10 nm, or greater than or equal to 600 nm and less than or equal to 750 nm, and light of the third example has a peak wavelength in the wavelength range of 400±10 nm, 440±10 nm, 470±10 nm, or greater than or equal to 600 nm and less than or equal to 750 nm.

A fourth example of the specific wavelength range is the wavelength range (from 390 nm to 470 nm) of excitation light that is used for observing fluorescence (fluorescence observation) emitted by a fluorescent material in a living body and that excites the fluorescent material.

A fifth example of the specific wavelength range is the wavelength range of infrared light. The wavelength range of the fifth example includes a wavelength range of greater than or equal to 790 nm and less than or equal to 820 nm or greater than or equal to 905 nm and less than or equal to 970 nm, and light of the fifth example has a peak wavelength in the wavelength range of greater than or equal to 790 nm and less than or equal to 820 nm or greater than or equal to 905 nm and less than or equal to 970 nm.

The endoscope processor apparatus 12 controls operations of the endoscope 10 through the connector 37b and the signal cable 36. In addition, based on the image signal acquired from the imaging element 28 of the endoscope 10 through the connector 37b and the signal cable 36, the endoscope processor apparatus 12 generates a moving image 38 that is a time-series image (example of a plurality of medical images) formed of time-series frame images 38a (see FIG. 2) including the photographic subject image. The frame rate of the moving image 38 is, for example, 30 fps (frame per second).

Furthermore, if the still image pick-up command unit 32 is operated in the handheld operating unit 21 of the endoscope 10, concurrently with the generation of the moving image 38, the endoscope processor apparatus 12 acquires one frame image 38a in the moving image 38 as the still image 39 in accordance with the timing of an imaging command.

The moving image 38 and the still image 39 are medical images obtained by capturing images of the inside of the subject, that is, a living body. In addition, if the moving image 38 and the still image 39 are images obtained with the above-described light in the specific wavelength range (special light), both are special light images. In addition, the endoscope processor apparatus 12 outputs the generated moving image 38 and the still image 39 to each of the display apparatus 13 and the medical image processing apparatus 14.

Note that the endoscope processor apparatus 12 may generate (acquire) the special light image having information on the above-described specific wavelength range, based on a usual light image obtained with the above-described white light. In this case, the endoscope processor apparatus 12 functions as a special light image acquiring unit. Then, the endoscope processor apparatus 12 obtains a signal in the specific wavelength range by performing calculation based on RGB color information of red, green, and blue or CMY color information of cyan, magenta, and yellow included in the usual light image.

Based on, for example, at least one of the usual light image obtained with the above-described white light or the special light image obtained with the above-described light in the specific wavelength range (special light), the endoscope processor apparatus 12 may generate a feature quantity image such as a known oxygen saturation image. In this case, the endoscope processor apparatus 12 functions as a feature quantity image generating unit. Note that each of the moving image 38 and the still image 39 including the above-described in-living-body image, the usual light image, the special light image, and the feature quantity image is a medical image obtained by converting results of imaging or measuring of a human body into an image for the purpose of image diagnosis or inspection.

The display apparatus 13 is connected to the endoscope processor apparatus 12 and displays the moving image 38 and the still image 39 input from the endoscope processor apparatus 12. A surgeon (physician) operates the insertion part 20 back and forth, for example, while viewing the moving image 38 displayed on the display apparatus 13, and, if a lesion or the like is found at the part to be observed, the surgeon (physician) operates the still image pick-up command unit 32 to capture a still image of the part to be observed for diagnosis, biopsy, or the like.

Configuration of Medical Image Processing Apparatus

The medical image processing apparatus 14 mainly reports a region of interest included in a time-series image to a surgeon, and, for example, a personal computer is used as the medical image processing apparatus 14 in this embodiment. In addition, a keyboard, a mouse, or the like connected to the personal computer via wired or wireless connection is used as the operating unit 15, and any monitor, such as a liquid crystal monitor that can be connected to the personal computer, is used as the display 16 (example of a display unit).

Figure 2:
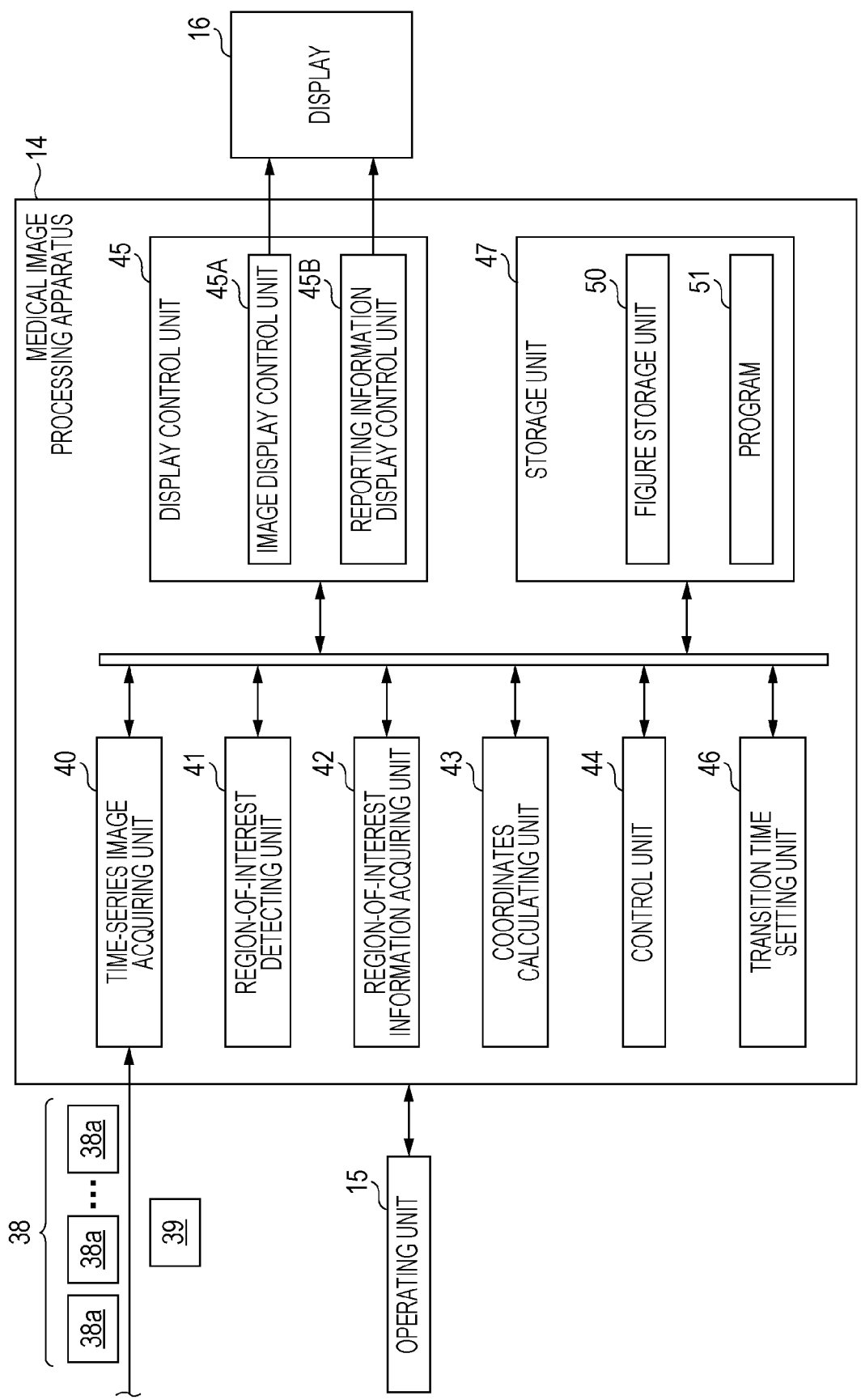
FIG. 2 is a block diagram illustrating an electric configuration of a medical image processing apparatus.

FIG. 2 is a block diagram illustrating an electric configuration of the medical image processing apparatus 14. The medical image processing apparatus 14 illustrated in FIG. 2 is mainly constituted by a time-series image acquiring unit 40, a region-of-interest detecting unit 41, a region-of-interest information acquiring unit 42, a coordinates calculating unit 43, a control unit 44, a display control unit 45, a transition time setting unit 46, and a storage unit 47.

Based on a program (medical image processing program) 51 stored in the storage unit 47, the control unit 44 generally controls the time-series image acquiring unit 40, the region-of-interest detecting unit 41, the region-of-interest information acquiring unit 42, the coordinates calculating unit 43, the display control unit 45, and the transition time setting unit 46 and functions as part of these units.

The storage unit 47 is a part that stores detection results obtained by the region-of-interest detecting unit 41 and stores a captured still image 39, and also stores information or the like related to various controls of a figure storage unit 50 that stores figures constituting the reporting information, a program 51, and the medical image processing apparatus 14.

The time-series image acquiring unit 40 acquires, from the endoscope processor apparatus 12 (FIG. 1), the moving image 38 (moving image 38 captured by the endoscope 10 in this example), formed of the time-series frame images 38a including a photographic subject image, by using an image input/output interface, which is not illustrated, connected to the endoscope processor apparatus 12 via wired or wireless connection. In addition, if the above-described still image 39 is captured while the moving image 38 is being captured by the endoscope 10, the time-series image acquiring unit 40 acquires the moving image 38 and the still image 39 from the endoscope processor apparatus 12.

Note that, instead of directly acquiring the moving image 38 from the endoscope processor apparatus 12, the time-series image acquiring unit 40 may acquire the moving image 38 via any information storage medium, such as a memory card or a hard disk apparatus. In addition, the time-series image acquiring unit 40 may acquire, via the Internet, the moving image 38 uploaded on a server, database, or the like on the Internet.

The region-of-interest detecting unit 41 is a part that detects a region of interest from the moving image 38 captured during observation of a body cavity. The region-of-interest detecting unit 41 calculates a feature quantity (an example of an image feature quantity) of the frame images 38a (or the frame images 38a decimated at certain intervals) of the moving image 38, includes a convolutional neural network (CNN) that performs recognition processing of the region of interest within an image, and calculates a feature quantity from color information, a pixel value gradient, or the like within the image. By using the calculated feature quantity, the region-of-interest detecting unit 41 detects the region of interest such as a lesion in the image.

As examples of the region of interest, there are a polyp, cancer, a colon diverticulum, inflammation, an endoscopic mucosal resection (EMR) scar, an endoscopic submucosal dissection (ESD) scar, a clipped part, a bleeding point, perforation, an atypical vessel, a treatment tool, and the like.

The region-of-interest detecting unit 41 can further acquire a recognition result of, for example, category classification as to whether the detected region of interest belongs to which of a plurality of categories about the lesion, such as "tumorous", "non-tumorous", and "others".

Note that the region-of-interest detecting unit 41 is not limited to the one that detects the region of interest by the CNN, but may detect the region of interest by analyzing a feature quantity such as the color, pixel value gradient, shape, or size the image through image processing.

If the region-of-interest detecting unit 41 detects the region of interest, the region-of-interest information acquiring unit 42 acquires region-of-interest information indicating the region of interest from the region-of-interest detecting unit 41. The region-of-interest information can be, for example, information of coordinates of a contour of the region of interest in the image.

The coordinates calculating unit 43 acquires the region-of-interest information from the region-of-interest information acquiring unit 42 and, based on the acquired region-of-interest information, calculates one or more sets of coordinates of interest indicating the position of the region of interest in the moving image 38. The coordinates calculating unit 43 calculates, for example, one or more sets of coordinates of interest on the contour of a polygon or a circle that surrounds a region of interest. As the one or more sets of coordinates of interest, sets of coordinates of vertexes of the polygon or sets of coordinates of midpoints of sides of the polygon may be calculated, or sets coordinates of points at which a circumference of the circle is equally divided into a plurality of parts may be calculated.

The transition time setting unit 46 acquires a feature quantity of the region of interest from the region-of-interest information acquiring unit 42 and sets a transition time for emphasis processing in accordance with the acquired feature quantity.

The display control unit 45 includes an image display control unit 45A and a reporting information display control unit 45B. The image display control unit 45A outputs the moving image 38 acquired by the time-series image acquiring unit 40 to the display 16 and causes the display 16 to display the moving image 38. That is, the display 16 sequentially displays a plurality of frame images 38a.

Based on a set of coordinates of interest calculated by the coordinates calculating unit 43, and based on the transition time set by the transition time setting unit 46, the reporting information display control unit 45B outputs reporting information constituted by a figure for reporting the region of interest to the display 16. Thus, in accordance with the transition time, the reporting information is superposed on the moving image 38 displayed on the display 16, and the position of the region of interest is emphasized by the reporting information. The reporting information display control unit 45B may superpose a plurality of figures, the number of which equals to the number of a plurality of sets of coordinates of interest or may superpose a circular figure or a rectangular figure obtained by connecting the plurality of sets of coordinates of interest with a straight line.

Medical Image Processing Method: First Embodiment

Figure 3:
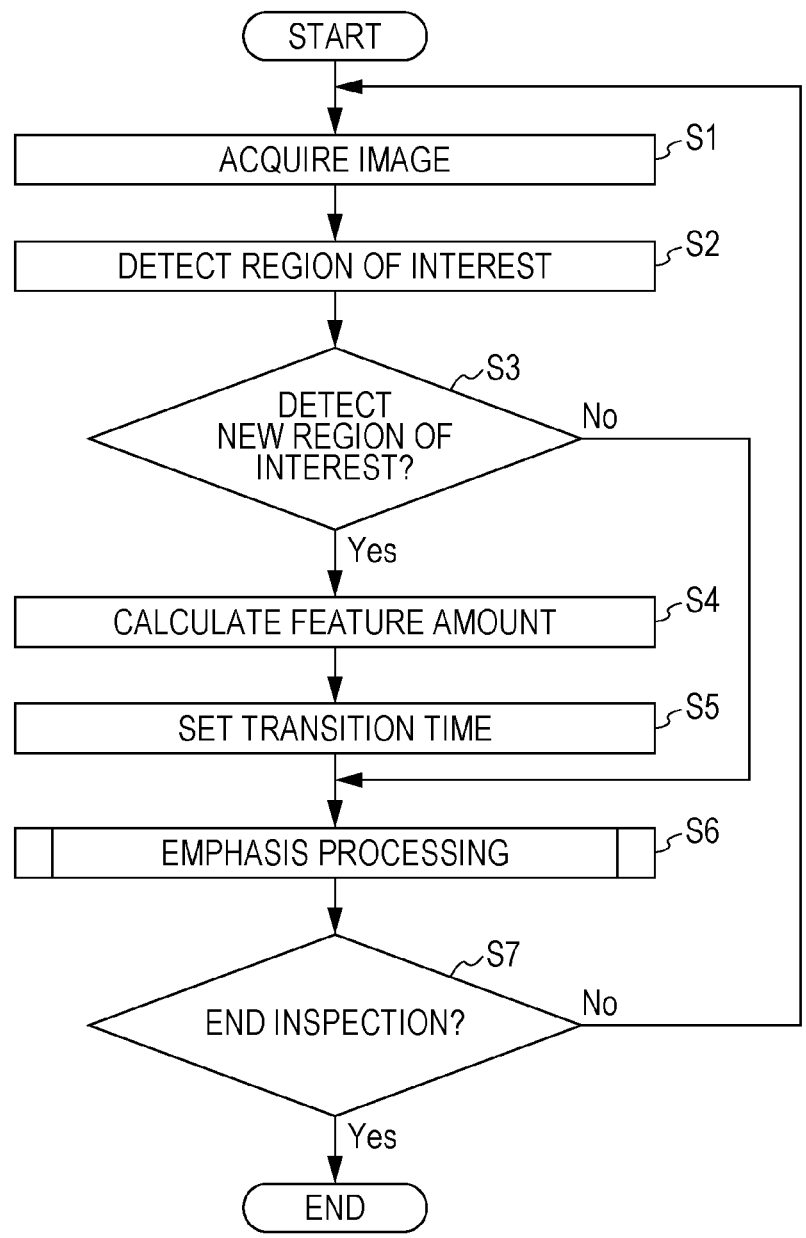
FIG. 3 is a diagram for describing a coordinates calculating unit and a reporting information display control unit.

A medical image processing method using the endoscope system 9 is described. FIG. 3 is a flowchart illustrating each process of the medical image processing method according to a first embodiment. The medical image processing method includes an image acquisition step (step S1), a region-of-interest detection step (step S2), a feature quantity calculation step (step S4), a transition time setting step (step S5), and an emphasis processing step (step S6).

In step S1, the time-series image acquiring unit 40 acquires a frame image 38a from the moving image 38 captured by the endoscope 10.

In step S2, the region-of-interest detecting unit 41 detects a region of interest from the frame image 38a acquired in step S1.

In step S3, the region-of-interest information acquiring unit 42 determines whether a new region of interest is detected in step S2. That is, the region-of-interest information acquiring unit 42 determines whether the region of interest detected in step S2 is a region of interest that is detected in a last-time frame image 38a and that is successively detected in the current frame image 38a or a new region of interest that is not detected in the last-time frame image 38a. If a new region of interest is detected in step S2, the process proceeds to step S4. If the region of interest detected in step S2 is not a new region of interest, or if a region of interest is not detected, the process proceeds to step S6.

In step S4, the region-of-interest information acquiring unit 42 (example of a feature quantity calculating unit) calculates a feature quantity of the new region of interest detected by the region-of-interest detecting unit 41. The feature quantity is calculated based on the visibility of the region of interest.

In step S5, the transition time setting unit 46 sets a transition time Ta of the new region of interest in accordance with the feature quantity calculated in step S4. The transition time Ta is set to a longer time as the visibility of the region of interest is relatively lower.

The transition time setting unit 46 stores, in association with the new region of interest, the set transition time Ta in a memory that is not illustrated. In addition, the transition time setting unit 46 acquires a time tf at which a time measuring unit that is not illustrated initially detects the new region of interest and stores, in association with the new region of interest, the acquired time tf in the memory that is not illustrated.

In step S6, the medical image processing apparatus 14 emphasizes the position of the region of interest included in the time-series image. That is, the image display control unit 45A causes the display 16 to display the frame image 38a. In addition, the reporting information display control unit 45B superposes reporting information constituted by a figure at the position of the region of interest detected in step S2 in the frame image 38a displayed on the display 16.

Herein, the image display control unit 45A causes the display 16 to display the frame image 38a in which the region of interest is detected in step S2. If the processing time from step S3 to step S6 is long, the image display control unit 45A may superpose the reporting information on frame images 38a after the frame image 38a in which the region of interest is detected in step S2.

Immediately after a lesion is detected, movement on a screen is large in many cases. Thus, in order to prevent missing, higher-level emphasis display is needed. On the other hand, after a specific time elapses from the detection and a user finds a region of interest, emphasis display may interrupt observation and is not preferable. Thus, in step S6, the reporting information display control unit 45B (example of an emphasis processing unit) emphasizes the position of the region of interest at a first emphasis level and, after the transition time has elapsed from emphasis at the first emphasis level, emphasizes the position of the region of interest at a second emphasis level relatively lower than the first emphasis level. Details of the emphasis processing will be described later.

In subsequent step S7, the control unit 44 determines if an endoscope inspection ends. If the inspection ends, the process in this flowchart ends. If the inspection does not end, substantially the same process from step S1 is repeated.

Emphasis Processing Step

Figure 4:
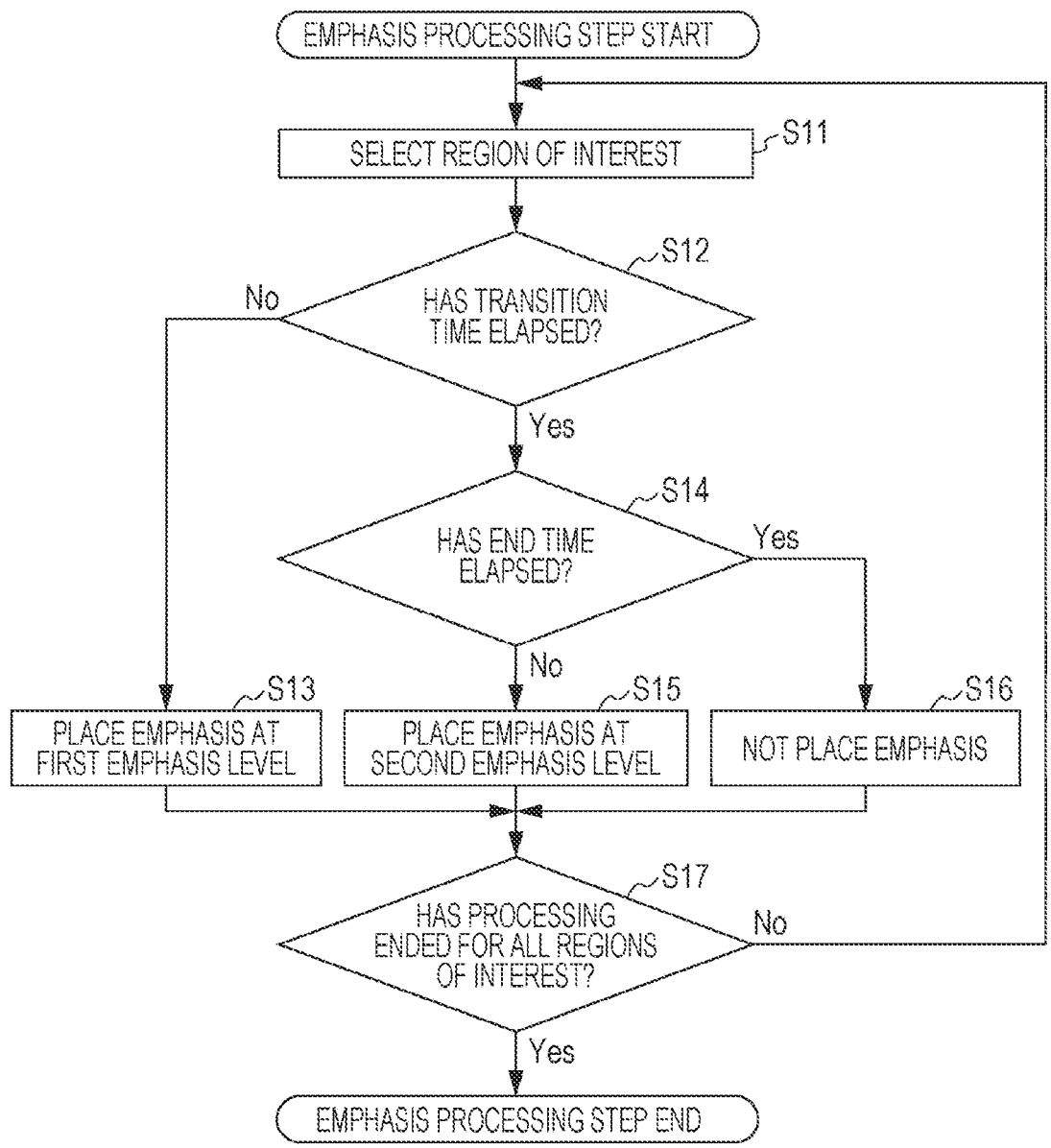
FIG. 4 is a flowchart illustrating details of an emphasis processing step.

FIG. 4 is a flowchart illustrating details of the emphasis processing step (step S6).

In step S11, the reporting information display control unit 45B selects one region of interest from among regions of interest detected in step S2.

In step S12, the reporting information display control unit 45B determines whether the transition time Ta has elapsed from the initial detection of the region of interest selected in step S11.

That is, the reporting information display control unit 45B reads, from the memory that is not illustrated, the transition time Ta associated with the region of interest selected in step S11 and the time tf at which the region of interest selected in S11 is initially detected. The reporting information display control unit 45B further reads a current time tc from the time measuring unit that is not illustrated. Then, the reporting information display control unit 45B calculates an elapsed time Tp=tc−tf from the initial detection of the region of interest selected in step S11 and compares the elapsed time Tp with the transition time Ta.

If the time from the initial detection of the region of interest is shorter than the transition time Ta, the process proceeds to step S13. In step S13, the reporting information display control unit 45B emphasizes the region of interest selected in step S11 at a first emphasis level LV1. In this manner, immediately after the detection, emphasis is placed at the first emphasis level LV1, which is a relatively high emphasis level, and thus, a surgeon can be prevented from missing the region of interest.

If the time from the initial detection of the region of interest is longer than or equal to the transition time Ta, the process proceeds to step S14. In step S14, the reporting information display control unit 45B determines whether an end time Te has elapsed from the initial detection of the region of interest selected in step S11. Herein, the end time Te=transition time Ta+fixed time Tb, and the reporting information display control unit 45B compares the elapsed time Tp with the end time Te. The fixed time Tb is stored in advance in the memory that is not illustrated. The fixed time Tb may be set to the same time as the transition time Ta.

If the time from the initial detection of the region of interest is shorter than the end time Te, the process proceeds to step S15. In step S15, the reporting information display control unit 45B emphasizes the region of interest selected in step S11 at a second emphasis level LV2. The second emphasis level LV2 is an emphasis level relatively lower than the first emphasis level LV1.

In this manner, after the transition time Ta has elapsed, emphasis is placed at the second emphasis level LV2, which is a relatively low emphasis level, and thus, appropriate emphasis display can be performed.

If the time from the initial detection of the region of interest is longer than or equal to the end time Te, the process proceeds to step S16. In step S16, the reporting information display control unit 45B ends emphasis of the region of interest selected in step S11. That is, after the end time Te has elapsed, the reporting information display control unit 45B does not emphasize the region of interest selected in step S11.

In this manner, since the emphasis processing is not performed after the end time Te has elapsed, observation of the region of interest found by a surgeon is not interrupted.

In subsequent step S17, the reporting information display control unit 45B determines whether the emphasis processing for all regions of interest detected in step S2 has ended. If the emphasis processing for all regions of interest has ended, the process in this flowchart ends. If the emphasis processing for all regions of interest has not ended, the process returns to step S1 to select a different region of interest, and substantially the same process is repeated.

Note that even a detected region that is detected once and for which the transition time Ta is set, a region of interest not detected in step S2 is not selected in step S11. That is, a region of interest not detected in step S2 is not subjected to emphasis processing regardless of the set transition time Ta. Thus, the region of interest that disappears from the screen is not subjected to emphasis processing, and observation of the moving image by a surgeon is not interrupted by unnecessary emphasis processing. In addition, the region of interest that is likely to be missed can be emphasized.

Display Examples of Emphasis Processing

Figure 5:
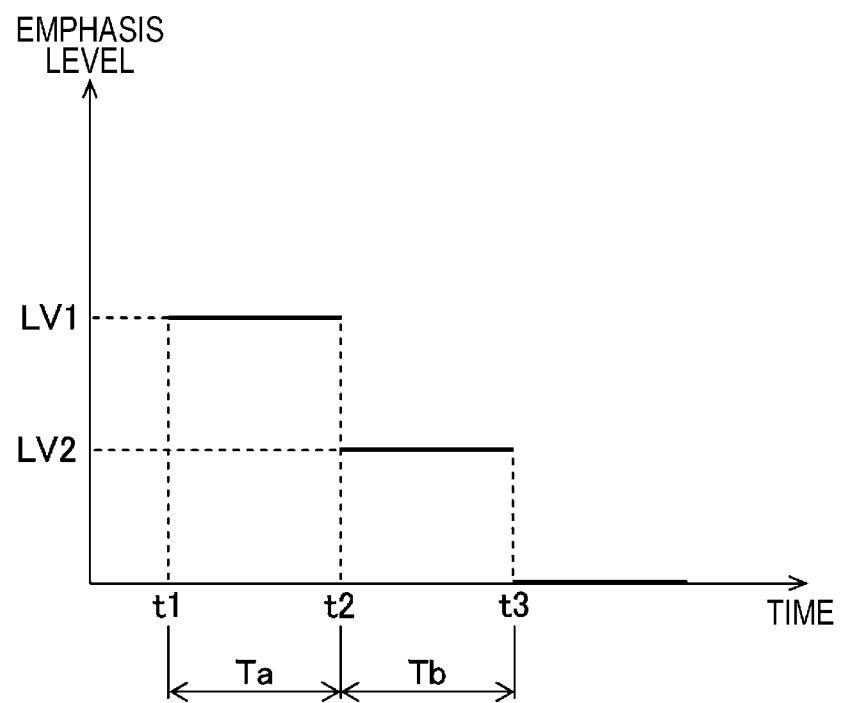
FIG. 5 illustrates transition of an emphasis level of a region of interest.

FIG. 5 illustrates an example of transition of an emphasis level of a region of interest. In the example illustrated in FIG. 5, a time t1 is a time at which the region of interest is detected. In addition, a time t2 is a time at which the transition time Ta has elapsed from the time t1. Furthermore, a time t3 is a time at which the end time Te (=Ta+Tb) has elapsed from the time t1.

Figure 6:
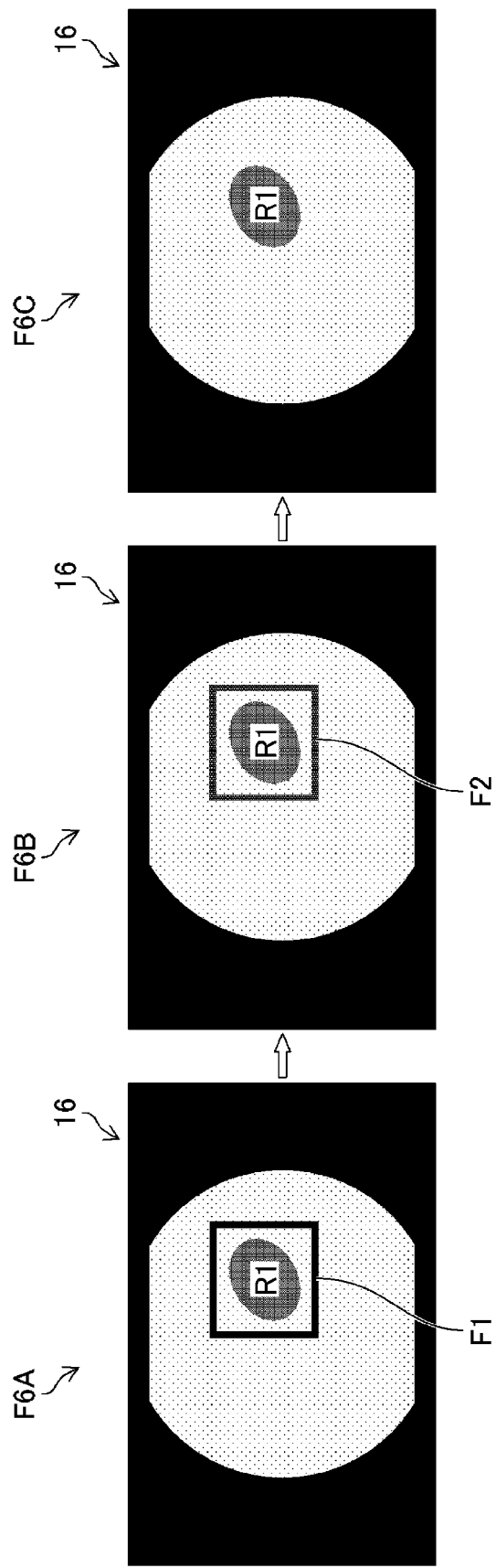
FIG. 6 illustrates an example of transition of emphasis display of a region of interest.

FIG. 6 illustrates an example of transition of emphasis display of a region of interest. F6A in FIG. 6 illustrates an example of an image displayed on the display 16 from the time t1 until the time t2. As illustrated in F6A, from the time t1 until the time t2, a region of interest R1 that is newly detected at the time t1 is emphasized by being surrounded by a rectangular figure F1. In this example, the figure F1 has a color at the first emphasis level LV1, and the position of the region of interest R1 is emphasized by the figure F1 at the first emphasis level LV1. In this manner, the newly detected region of interest R1 is emphasized at the first emphasis level LV1, and thus, a surgeon can be prevented from missing the region of interest.

F6B in FIG. 6 illustrates an example of an image displayed on the display 16 from the time t2 until the time t3. As illustrated in F6B, from the time t2 until the time t3, a region of interest R1 that is successively detected from the time t1 is emphasized by being surrounded by a rectangular figure F2. The figure F2 has a color at the second emphasis level LV2, and the position of the region of interest R1 is emphasized by the figure F2 at the second emphasis level LV2.

After the transition time Ta has elapsed, necessity for reporting (enhancing) the region of interest R1 is decreased. Thus, after the transition time Ta has elapsed, the region of interest R1 is emphasized at the second emphasis level LV2, which is the emphasis level lower than the first emphasis level LV1. This enables emphasis display appropriate for each occasion.

By setting the transition time Ta in accordance with features of the region of interest, emphasis display can be switched at an optimal time for each region of interest. Herein, a longer transition time is set as the evaluated visibility of the region of interest is lower. As the visibility is lower, it is more likely that a surgeon is delayed in finding the region of interest. Thus, display at the first emphasis level LV1 for a longer time can contribute to prevention of missing. In contrast, a lesion with high visibility can be found by a surgeon with ease, by switching display at the first emphasis level LV1 to emphasis at the second emphasis level LV2 in a short time, observation by a surgeon can be less adversely affected.

F6C in FIG. 6 illustrates an example of an image displayed on the display 16 at and after the time t3. As illustrated in F6C, the region of interest R1 is not emphasized at and after the time t3. After the end time Te has elapsed, it may be unnecessary to report the region of interest R1. Thus, since the region of interest R1 is not emphasized, observation of the moving image by a surgeon can be prevented from being interrupted.

Variations of Changes in Emphasis Levels

In the example illustrated in FIG. 6, emphasis at the first emphasis level LV1 and emphasis at the second emphasis level LV2 are implemented by changing the color of a figure that is superposed and displayed, the emphasis level can be changed in the following manners.

Figure 7:
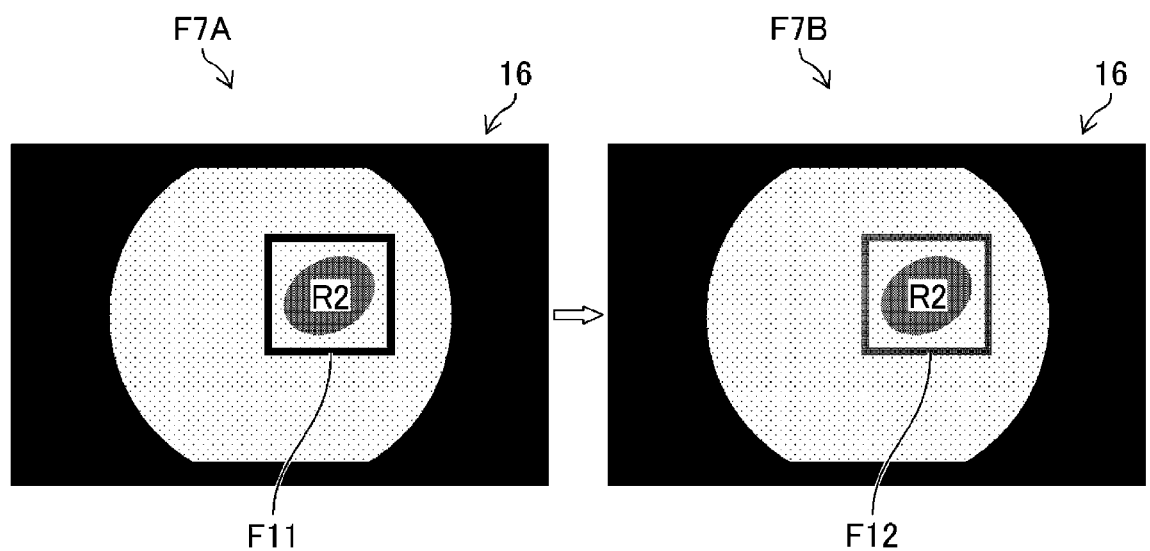
FIG. 7 illustrates an example of a manner for changing an emphasis level of a region of interest by changing the color of a figure.

FIG. 7 illustrates an example of a manner for changing an emphasis level of a region of interest by changing the color of a figure. In F7A in FIG. 7, a region of interest R2 is emphasized by being surrounded by a rectangular figure F11. The figure F11 has a concentration at the first emphasis level LV1, and the position of the region of interest R2 is emphasized at the first emphasis level LV1 by the figure F11. In F7B in FIG. 7, the region of interest R2 is emphasized by being surrounded by a rectangular figure F12. The figure F12 has a concentration at the second emphasis level LV2, and the position of the region of interest R2 is emphasized at the second emphasis level LV2 by the figure F12. In this manner, by placing emphasis by using the figure F11 and the figure F12, the emphasis level can be changed.

Figure 8:
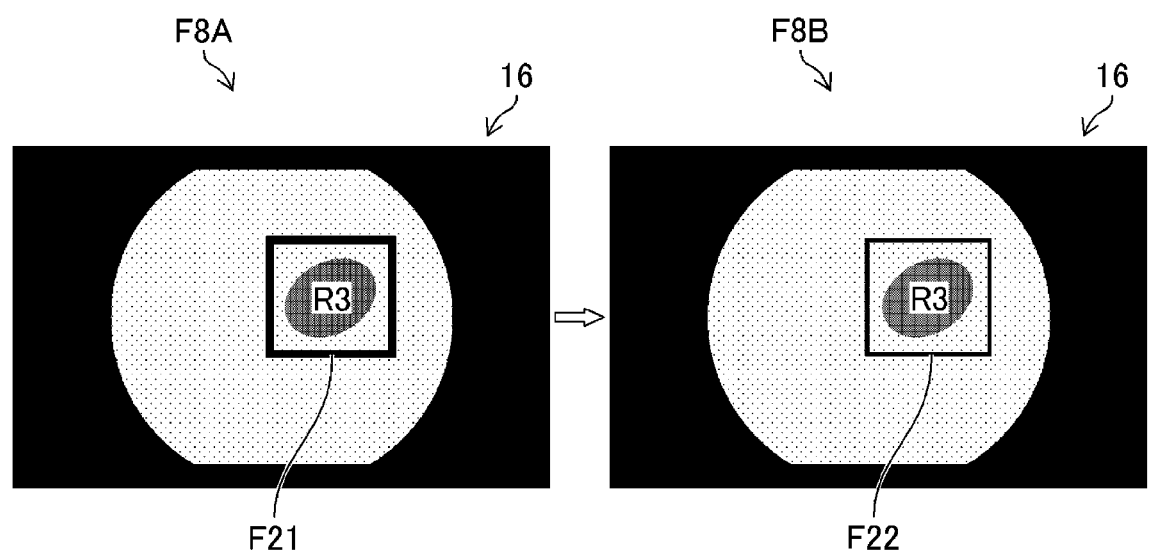
FIG. 8 illustrates an example of a manner for changing an emphasis level of a region of interest by changing the line thickness of a figure.

FIG. 8 illustrates an example of a manner for changing an emphasis level of a region of interest by changing the line thickness of a figure. In F8A in FIG. 8, a region of interest R3 is emphasized by being surrounded by a rectangular figure F21. The figure F21 has a line thickness at the first emphasis level LV1, and the position of the region of interest R3 is emphasized at the first emphasis level LV1 by the figure F21. In F8B in FIG. 8, the region of interest R3 is emphasized by being surrounded by a rectangular figure F22. The figure F22 has a line thickness at the second emphasis level LV2, and the position of the region of interest R3 is emphasized at the second emphasis level LV2 by the figure F22. In this manner, by placing emphasis by using the figure F21 and the figure F22, the emphasis level can be changed.

Figure 9:
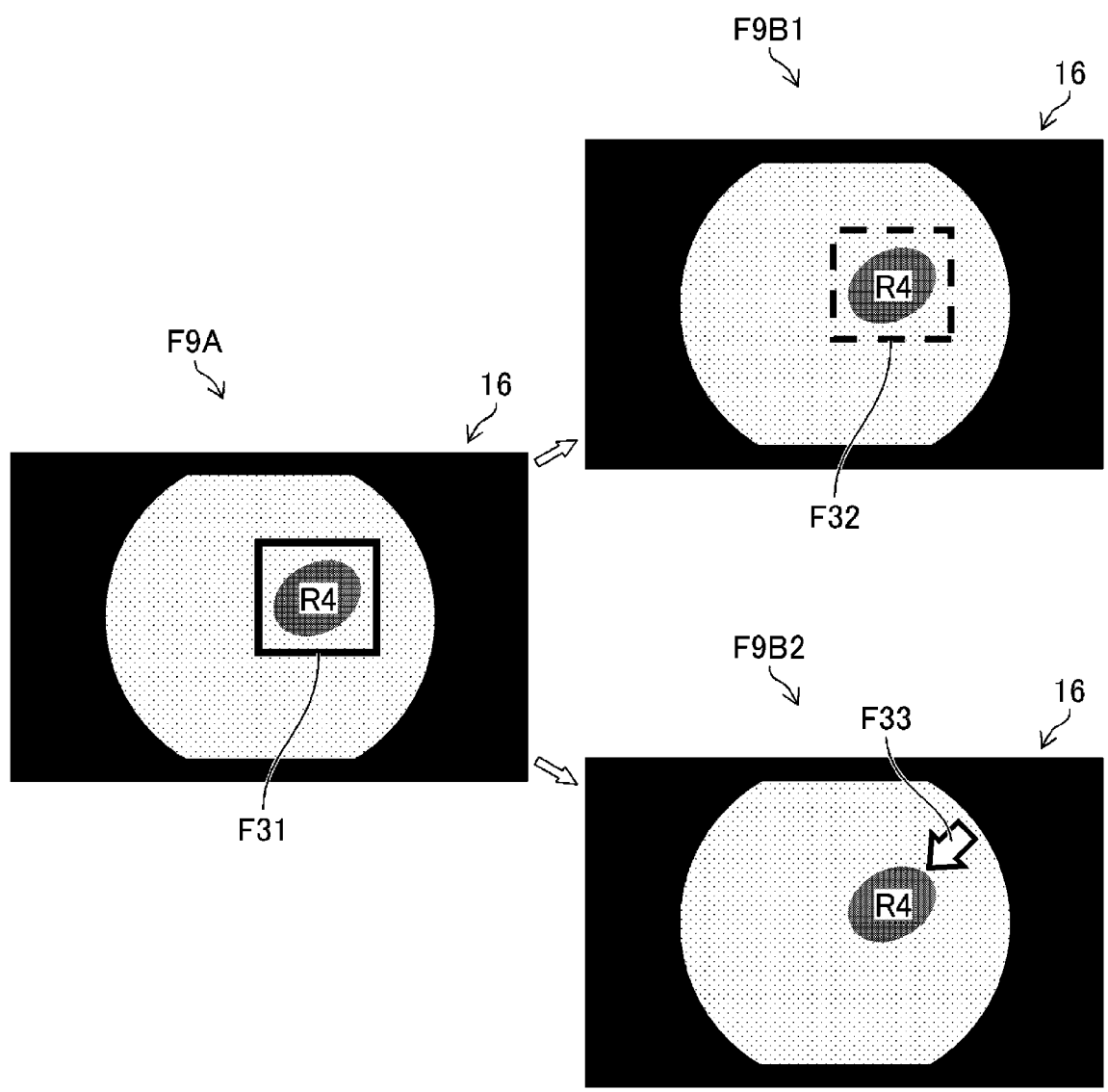
FIG. 9 illustrates an example of a manner for changing an emphasis level of a region of interest by changing the shape of a figure.

FIG. 9 illustrates an example of a manner for changing an emphasis level of a region of interest by changing the shape of a figure. In F9A in FIG. 9, a region of interest R4 is emphasized by being surrounded by a solid-line rectangular figure F31. The figure F31 has a shape at the first emphasis level LV1, and the position of the region of interest R4 is emphasized at the first emphasis level LV1 by the figure F31. In F9B1 in FIG. 9, the region of interest R4 is emphasized by being surrounded by a broken-line rectangular figure F32. The figure F32 has a shape at the second emphasis level LV2, and the position of the region of interest R4 is emphasized at the second emphasis level LV2 by the figure F32. In this manner, by placing emphasis by using the figure F31 and the figure F32, the emphasis level can be changed.

In F9B2 in FIG. 9, the region of interest R4 is emphasized by being indicated by an arrow-like figure F33. The figure F33 has a shape at the second emphasis level LV2, and the position of the region of interest R4 is emphasized at the second emphasis level LV2 by the figure F33. Thus, by placing emphasis by using the figure F31 and the figure F33, the emphasis level can be changed.

Figure 10:
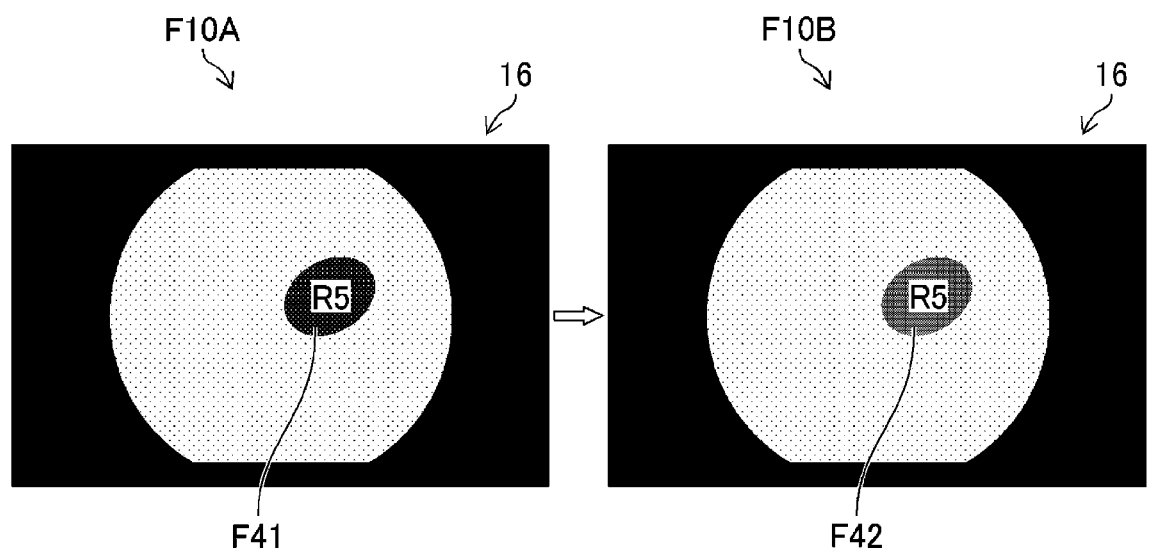
FIG. 10 illustrates an example of a manner for changing an emphasis level of a region of interest by changing the concentration of a figure.

FIG. 10 illustrates an example of a manner for changing an emphasis level of a region of interest by changing the concentration of a figure. Herein, the figure is superposed on the region of interest. In F10A in FIG. 10, a region of interest R5 is emphasized by a figure F41 superposed thereon. The figure F41 has a concentration at the first emphasis level LV1, and the position of the region of interest R5 is emphasized at the first emphasis level LV1 by the figure F41. In F10B in FIG. 10, the region of interest R5 is emphasized by a figure F42 superposed thereon. The figure F42 has a concentration at the second emphasis level LV2, and the position of the region of interest R5 is emphasized at the second emphasis level LV2 by the figure F42. In this manner, by placing emphasis by using the figure F41 and the figure F42, the emphasis level can be changed.

A plurality of parameters among the color, concentration, line thickness, and shape can be changed, and the figures at the first emphasis level LV1 and the figures at the second emphasis level LV2 illustrated in FIGS. 6 to 10 can be used in combination as appropriate.

Figure 11:
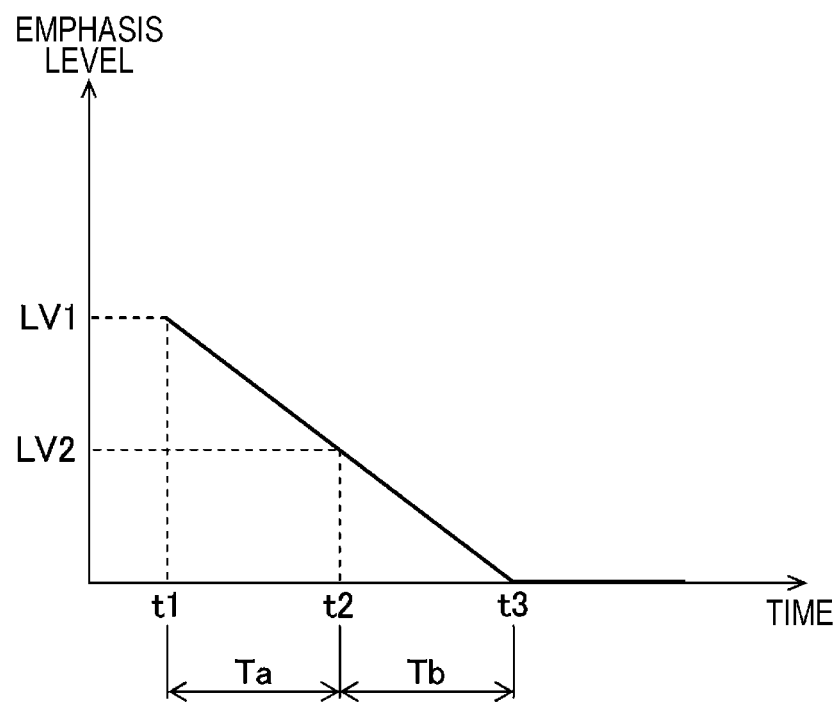
FIG. 11 illustrates continuous transition of an emphasis level of a region of interest.

Although the emphasis level is changed in a stepwise manner in the example illustrated in FIG. 5, the emphasis level may also be changed continuously. FIG. 11 illustrates continuous transition of an emphasis level of a region of interest. The times t1, t2, and t3 are substantially the same as those in FIG. 5.

In the example illustrated in FIG. 11, from emphasis at the first emphasis level until the transition time Ta elapses (from the time t1 until the time t2), emphasis is placed while the emphasis level is relatively, gradually decreased, and from emphasis at the second emphasis level LV2 until the fixed time Tb elapses (from the time t2 until the time t3), emphasis is implemented while the emphasis level is relatively, gradually decreased. The emphasis level may be changed in this manner.

Note that emphasis may be placed while the emphasis level is relatively, gradually decreased from the time t1 until the time t2, and emphasis may be placed at the second emphasis level LV2 from the time t2 until the time t3. Alternatively, emphasis may be placed at the first emphasis level LV1 from the time t1 until the time t2, and emphasis may be placed while the emphasis level is relatively, gradually decreased from the time t2 until the time t3.

Feature Quantity and Transition Time

In this embodiment, the region-of-interest information acquiring unit 42 calculates the feature quantity based on the visibility of the region of interest, and the transition time setting unit 46 sets the longer transition time Ta as the visibility is relatively lower. However, the feature quantity may be calculated based on other features of the region of interest, and the transition time may be set.

For example, the feature quantity may be calculated based on the size of the region of interest in an image. In this case, the transition time is set based on the size of the region of interest in the image. As the region of interest is smaller, it is more likely that a surgeon is delayed in finding the region of interest. Thus, as the region of interest is relatively smaller, the transition time Ta is preferably set to a longer time.

The feature quantity may also be calculated based on the position of the region of interest in an image. In this case, the transition time is set based on the position of the region of interest in the image. As the position of the region of interest is closer to an edge (periphery) of the image, it is more likely that a surgeon pays low attention, that the region of interest tends to be outside the image, and that the surgeon is delayed in finding the region of interest. Thus, as the position of the region of interest is relatively closer to the periphery of the image, the transition time Ta is preferably set to a longer time.

The feature quantity may also be calculated based on the luminance of the region of interest or a difference between the luminance of the region of interest and the luminance of an outside region of the region of interest. In this case, the transition time is set based on the luminance of the region of interest or a difference between the luminance of the region of interest and the luminance of an outside region of the region of interest. As the region of interest is darker, or the difference in luminance from the periphery is smaller, it is more likely that a surgeon is delayed in finding the region of interest. Thus, as the luminance of the region of interest is relatively smaller, or the difference between the luminance of the region of interest and the luminance of an outside region of the region of interest is relatively smaller, the transition time Ta is preferably set to a longer time. The luminance of the region of interest and the luminance of an outside region of the region of interest can be calculated based on a statistical index such as an average or a median of the luminance.

The feature quantity may also be calculated based on the color information of the region of interest or a difference (distance in a color space) between the color information of the region of interest and the color information of an outside region of the region of interest. In this case, the transition time is set based on the color information of the region of interest or a difference (distance in a color space) between the color information of the region of interest and the color information of an outside region of the region of interest. As the saturation (example of the color information) of the region of interest is lower, or the color difference from the periphery is smaller, it is more likely that a surgeon is delayed in finding the region of interest. Thus, as the saturation of the region of interest is relatively lower, or the difference between the saturation of the region of interest and the saturation of an outside region of the region of interest is relatively smaller, the transition time Ta is preferably set to a longer time.

Furthermore, the feature quantity may also be calculated based on the movement amount of the region of interest or the movement direction of the region of interest. In this case, the transition time is set based on the movement amount of the region of interest or the movement direction of the region of interest. As the movement amount of the region of interest is larger, it is more likely that a surgeon is delayed in finding the region of interest. Thus, as the movement amount of the region of interest is larger, the transition time Ta is preferably set to a longer time. In addition, if the movement direction of the region of interest is toward the edge of the screen, it is likely that a surgeon is delayed in finding the region of interest. Thus, if the movement direction of the region of interest is toward the edge of the screen, the transition time Ta is preferably set to a longer time than that set if the movement direction of the region of interest is toward the center of the screen.

Second Embodiment

In the first embodiment, upon detection of a new region of interest, the feature quantity of the region of interest is calculated, and, in accordance with the calculated feature quantity, the transition time Ta of the region of interest is set. Thus, the transition time Ta is determined at the time point of detection, and future change in the region of interest caused by, for example, movement of the endoscope 10, is not supported. In contrast, the transition time is reset in accordance with the feature quantity of the region of interest in a second embodiment.

Figure 12:
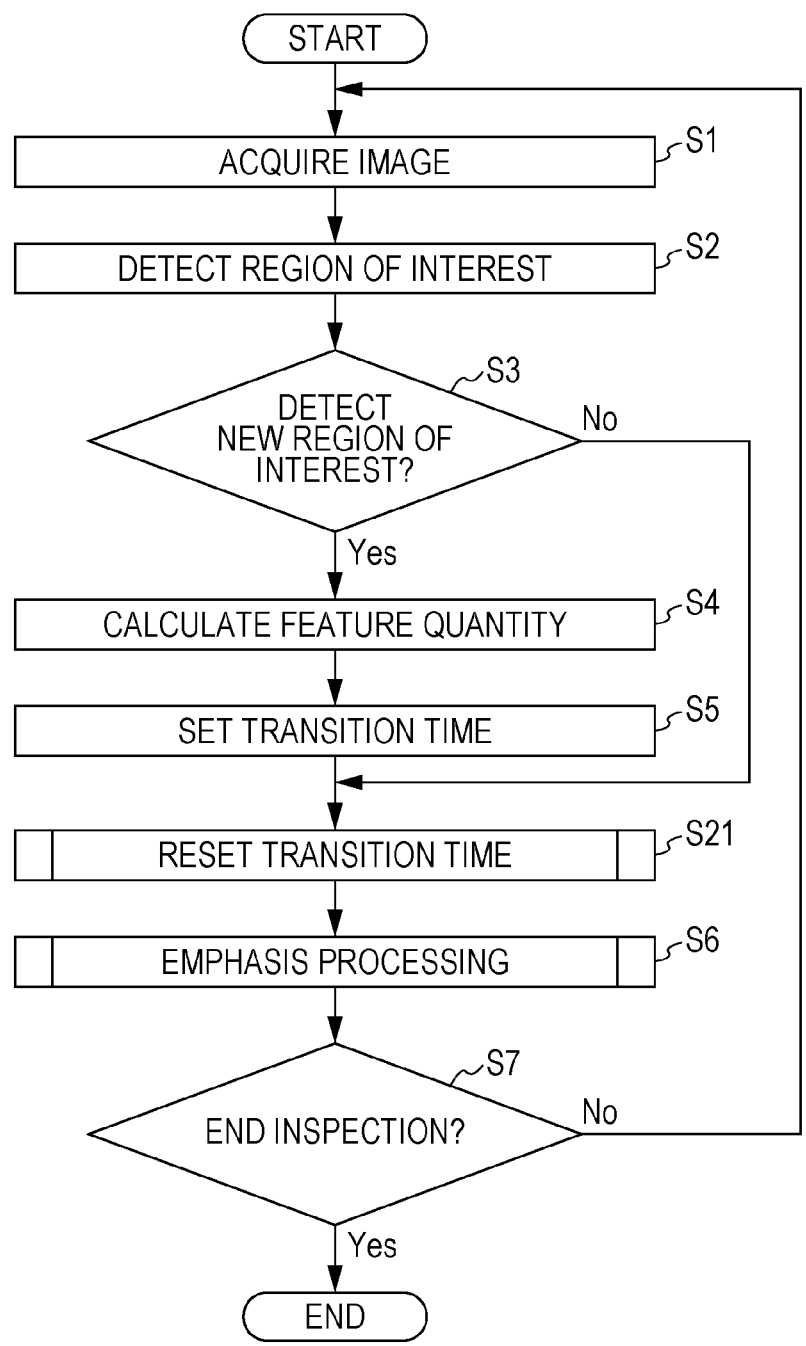
FIG. 12 is a flowchart illustrating each process of a medical image processing method.

A medical image processing method according to the second embodiment is described. FIG. 12 is a flowchart illustrating each process of the medical image processing method according to the second embodiment. Note that parts common to the flowchart illustrated in FIG. 3 are dented by the same reference numerals, and detailed description thereof is omitted.

The medical image processing method according to the second embodiment includes a transition time resetting step (step S21) between the transition time setting step (step S5) and the emphasis processing step (step S6).

Transition Time Resetting Step

Figure 13:
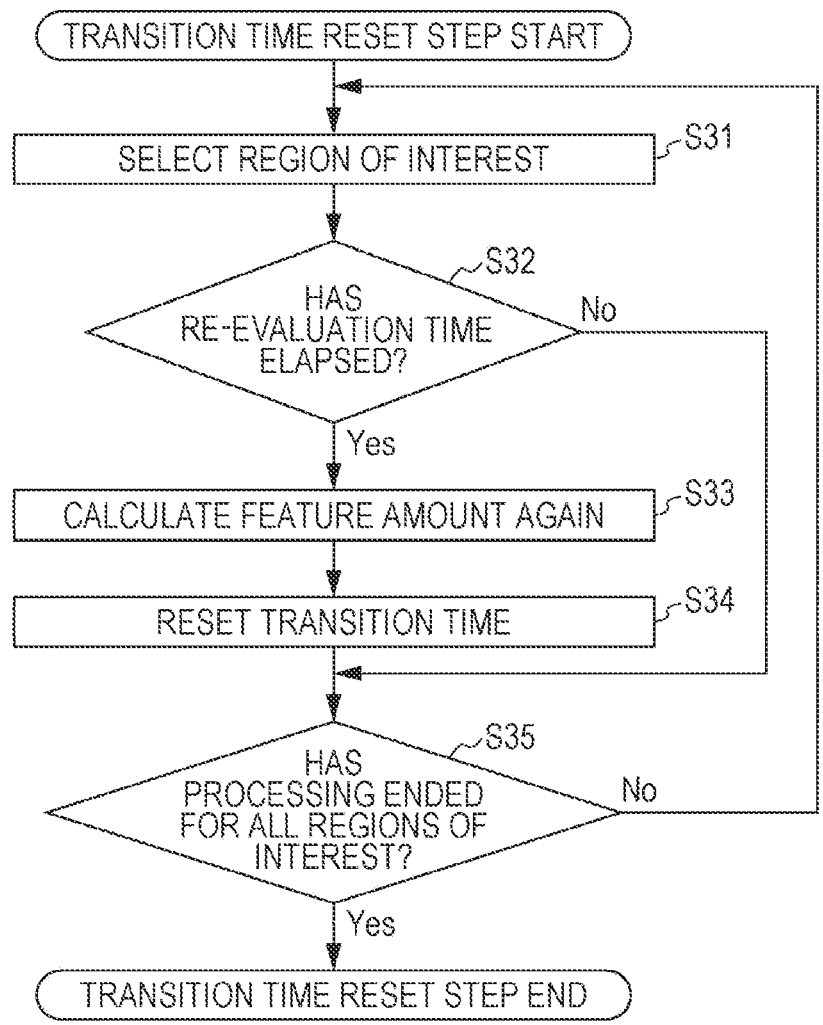
FIG. 13 is a flowchart illustrating details of a transition time resetting step.

FIG. 13 is a flowchart illustrating details of the transition time resetting step (step S21).

In step S31, the transition time setting unit 46 selects one region of interest from among regions of interest detected in step S2.

In step S32, the transition time setting unit 46 determines whether a re-evaluation time Tr has elapsed from the initial detection of the region of interest selected in step S31.

That is, the transition time setting unit 46 reads, from the memory that is not illustrated, the preset re-evaluation time Tr and the time tf at which the region of interest selected in S31 is initially detected. The transition time setting unit 46 further reads a current time tc from the time measuring unit that is not illustrated. Then, the transition time setting unit 46 calculates an elapsed time Tp=tc−tf from the initial detection of the region of interest selected in step S31 and compares the elapsed time Tp with the re-evaluation time Tr.

If the re-evaluation time Tr has not elapsed, the process proceeds to step S35. On the other hand, if the re-evaluation time Tr has elapsed, the process proceeds to step S33. In step S33, the region-of-interest information acquiring unit 42 calculates again the feature quantity of the region of interest selected in step S31. The feature quantity is calculated based on, for example, the visibility of the region of interest. Note that the feature quantity may also be calculated based on other features of the region of interest.

In subsequent step S34, the transition time setting unit 46 resets the transition time of the region of interest selected in step S31 in accordance with the feature quantity that is calculated again in step S33. The reset transition time is Tar. The transition time Tar is set to a longer time, for example, as the visibility of the region of interest is relatively lower.

The transition time setting unit 46 stores the reset transition time Tar in the memory that is not illustrated in association with the region of interest selected in step S31.

In step S35, the transition time setting unit 46 determines whether the emphasis processing for all regions of interest detected in step S2 has ended. If the emphasis processing for all regions of interest has ended, the process in this flowchart ends. If the emphasis processing for all regions of interest has not ended, the process returns to step S31 to select a different region of interest, and substantially the same process is repeated.

In the above manner, the transition time is reset. In the emphasis processing step in step S6, the emphasis processing is performed based on the reset transition time Tar.

Figure 14:
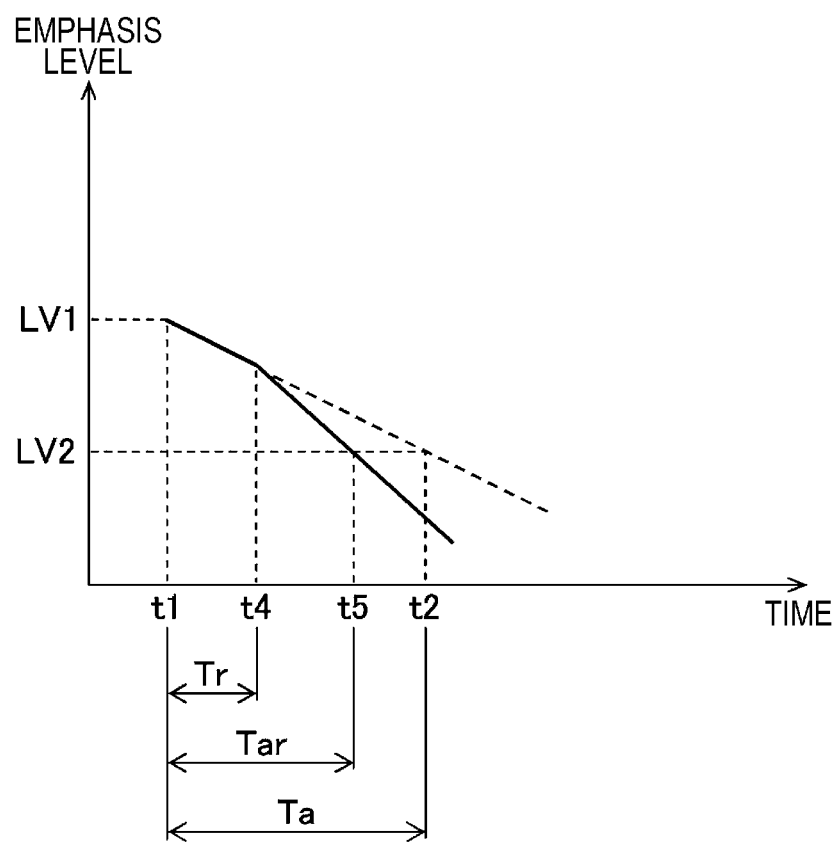
FIG. 14 illustrates an example of transition of an emphasis level of a region of interest.

FIG. 14 illustrates an example of transition of an emphasis level of a region of interest in this embodiment. A time t1 is a time at which the region of interest is detected. In addition, a time t2 is a time at which the initially set transition time Ta has elapsed from the time t1.

A time t4 is a time at which the re-evaluation time Tr has elapsed from the time t1. Herein, the transition time Tar is reset at the time t4. A time t5 is a time at which the reset transition time Tar has elapsed from the time t1.

In this manner, in the example illustrated in FIG. 14, the reset transition time Tar is a shorter time than the initial transition time Ta. Depending on the feature quantity of the region of interest at the time t4, the reset transition time Tar may be a longer time than the initial transition time Ta.

According to this embodiment, even if the feature quantity of the region of interest varies over time, the transition time can be set appropriately. For example, if the size of the region of interest in an image is small at the time point of detection of the region of interest, in many cases, the size of the region of interest in the image may be later increased by a surgeon's operation of the endoscope 10. In such a case, there is a problem that a comparatively long transition time that is set at the time point of detection may become inappropriate.

According to this embodiment, since the transition time is reset to a short time through re-evaluation of the feature quantity of the region of interest, such a problem can be solved. In contrast, in a case where the visibility is high at the time point of detection of the region of interest and is decreased for some reason, the transition time can be reset to a longer time. The re-evaluation of the feature quantity is not necessarily once and may be performed a number of times at fixed time intervals or at every frame.

Note that the transition time setting unit 46 may reset the fixed time Tb based on the feature quantity of the region of interest during the transition time resetting step.

Miscellaneous

The above medical image processing method can be configured as a program causing a computer to execute each step, and a non-transitory recording medium such as a compact disk-read only memory (CD-ROM) storing this program may also be configured.

Although the endoscope processor apparatus 12 and the medical image processing apparatus 14 are different apparatuses in the above embodiments, the endoscope processor apparatus 12 and the medical image processing apparatus 14 may also be constituted as an integrated apparatus, and the functions of the medical image processing apparatus 14 may be provided in the endoscope processor apparatus 12.

In addition, a hardware structure of a processing unit that performs various processes of the endoscope processor apparatus 12 and the medical image processing apparatus 14 is any of the following various processors. Various processors include a central processing unit (CPU) that is a general-purpose processor functioning as various processing units by executing software (programs), a graphics processing unit (GPU) that is a processor specialized in image processing, a programmable logic device (PLD) that is a processor in which the circuit configuration is changeable after manufacture, such as field programmable gate array (FPGA), a dedicated electric circuit that is a processor having a circuit configuration that is specially designed to execute specific processing, such as an application specific integrated circuit (ASIC), and the like.

One processing unit may be constituted by one of these various processors, or may be constituted by two or more processors of the same type or different types (e.g., a combination of a plurality of FPGAs, a combination of a CPU and an FPGA, or a combination of a CPU and a GPU). In addition, a plurality of processing units may be configured as one processor. As a first example for configuring a plurality of processing units as one processor, one or more CPUs and software may be combined to configure one processor, and this processor may function as a plurality of processing units, as typified by a computer such as a client or a server. As a second example, a processor may be used that implements the functions of the entire system including a plurality of processing units as one integrated circuit (IC) chip, as typified by a system on chip (SoC) or the like. In this manner, various processing units are constituted by one or more of various processors as a hardware structure.

Furthermore, the hardware structure of these various processors is more specifically is electric circuitry obtained by combining circuit elements such as semiconductor elements.

The technical scope of the present invention is not limited to the scope described in the above embodiments, and configurations or the like in each embodiment may be combined as appropriate between the embodiments without departing from the spirit of the present invention.

REFERENCE SIGNS LIST

9 endoscope system
10 endoscope
11 light source apparatus
12 endoscope processor apparatus
13 display apparatus
14 medical image processing apparatus
15 operating unit
16 display
20 insertion part
21 handheld operating unit
22 universal cord
25 soft part
26 bending part
27 distal end part
28 imaging element
29 bending operation knob
30 air/water supply button
31 suction button
32 still image pick-up command unit
33 treatment tool introduction port
35 light guide
36 signal cable
37a connector
37b connector
38 moving image
38a frame image
39 still image
40 time-series image acquiring unit
41 region-of-interest detecting unit
42 region-of-interest information acquiring unit
43 coordinates calculating unit
44 control unit
45 display control unit
45A image display control unit
45B reporting information display control unit
46 transition time setting unit
47 storage unit
50 figure storage unit
51 program F1 to F42 figure
R1 to R5 region of interest
S1 to S35 step of medical image processing method

What is claimed is:

1. A medical image processing apparatus comprising one or more processors that are configured to:
   emphasize a position of a region of interest included in a plurality of medical images sequentially displayed on a display unit; and
   set a transition time in accordance with a feature quantity of the region of interest,
   wherein the one or more processors emphasize the position of the region of interest at a first emphasis level and, after the transition time has elapsed from emphasis at the first emphasis level, emphasize the position of the region of interest at a second emphasis level relatively lower than the first emphasis level.

2. The medical image processing apparatus according to claim 1, wherein the one or more processors are further configured to:
   acquire the plurality of medical images;
   detect the region of interest from the medical images; and
   calculate the feature quantity of the region of interest.

3. The medical image processing apparatus according to claim 1, wherein the one or more processors are further configured to:
   cause the display unit to sequentially display the plurality of medical images, wherein the position of the region of interest at the first emphasis level during the transition time.

4. The medical image processing apparatus according to claim 1,
   wherein the feature quantity is calculated based on visibility of the region of interest.

5. The medical image processing apparatus according to claim 4,
   wherein the one or more processors set the transition time to a longer time as the visibility of the region of interest is relatively lower.

6. The medical image processing apparatus according to claim 1,
   wherein the feature quantity is calculated based on a size of the region of interest in the medical images.

7. The medical image processing apparatus according to claim 6,
   wherein the one or more processors set the transition time to a longer time as the size of the region of interest in the medical images is relatively smaller.

8. The medical image processing apparatus according to claim 1,
   wherein the feature quantity is calculated based on a position of the region of interest in the medical images.

9. The medical image processing apparatus according to claim 8,
   wherein the one or more processors set the transition time to a longer time as the position of the region of interest in the medical images is relatively closer to a periphery.

10. The medical image processing apparatus according to claim 1,
    wherein the feature quantity is calculated based on luminance of the region of interest or a difference between the luminance of the region of interest and luminance of an outside region of the region of interest.

11. The medical image processing apparatus according to claim 10,
    wherein the one or more processors set the transition time to a longer time as the luminance of the region of interest is lower, or the difference between the luminance of the region of interest and the luminance of the outside region of the region of interest is smaller.

12. The medical image processing apparatus according to claim 1,
    wherein the feature quantity is calculated based on color information of the region of interest or a difference between the color information of the region of interest and color information of an outside region of the region of interest.

13. The medical image processing apparatus according to claim 12,
    wherein the one or more processors set the transition time to a longer time as a difference between a color space of the region of interest and a color space of the outside region of the region of interest is smaller.

14. The medical image processing apparatus according to claim 1,
    wherein the feature quantity is calculated based on a movement amount of the region of interest or a movement direction of the region of interest.

15. The medical image processing apparatus according to claim 14,
    wherein the one or more processors set the transition time to a longer time as the movement amount of the region of interest is larger.

16. The medical image processing apparatus according to claim 1,
    wherein the one or more processors reset the transition time in accordance with the feature quantity of the region of interest from emphasis at the first emphasis level until the transition time elapses.

17. The medical image processing apparatus according to claim 1,
    wherein the one or more processors place emphasis at the first emphasis level from emphasis at the first emphasis level until the transition time elapses.

18. The medical image processing apparatus according to claim 1,
    wherein the one or more processors place emphasis while relatively, gradually decreasing an emphasis level from emphasis at the first emphasis level until the transition time elapses.

19. The medical image processing apparatus according to claim 1,
    wherein the one or more processors end emphasis when a fixed time elapses from emphasis at the second emphasis level.

20. The medical image processing apparatus according to claim 19,
    wherein the one or more processors place emphasis at the second emphasis level from emphasis at the second emphasis level until the fixed time elapses.

21. The medical image processing apparatus according to claim 19,
    wherein the one or more processors place emphasis while relatively, gradually decreasing an emphasis level from emphasis at the second emphasis level until the fixed time elapses.

22. An endoscope system comprising:
    the medical image processing apparatus according to claim 1;
    an endoscope that captures the plurality of medical images; and
    the display unit.

23. A medical image processing method comprising:
enhancing a position of a region of interest included in a plurality of medical images sequentially displayed on a display unit; and
setting a transition time in accordance with a feature quantity of the region of interest,
wherein, the position of the region of interest is emphasized at a first emphasis level and, after the transition time has elapsed from emphasis at the first emphasis level, the position of the region of interest is emphasized at a second emphasis level relatively lower than the first emphasis level.

24. A non-transitory computer-readable recording medium causing a computer to execute the medical image processing method according to claim 23 upon the computer reading a command stored in the recording medium.

* * * * *